(12) United States Patent
Hurry et al.

(10) Patent No.: US 6,435,423 B2
(45) Date of Patent: Aug. 20, 2002

(54) GEL TYPE VAPOR RELEASE DEVICE

(75) Inventors: Simon Hurry, Ascot; Jonathan L. Williams, London, both of (GB)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/837,910

(22) Filed: Apr. 19, 2001

Related U.S. Application Data

(63) Continuation of application No. PCT/IB99/01721, filed on Oct. 20, 1999.

(51) Int. Cl.[7] .................................................. A24F 25/00
(52) U.S. Cl. .......................................... 239/34; 239/60
(58) Field of Search .............................. 239/34, 44, 45, 239/47, 60, 145, 309

(56) References Cited

U.S. PATENT DOCUMENTS

| | | | |
|---|---|---|---|
| 4,419,326 A | 12/1983 | Santini | 422/4 |
| 4,739,928 A | 4/1988 | ONeil | 239/45 |
| 4,798,288 A | 1/1989 | Holzner | 206/222 |
| 4,915,301 A | 4/1990 | Munteanu | 239/45 |

FOREIGN PATENT DOCUMENTS

| | | |
|---|---|---|
| EP | 0 835 666 | 4/1998 |
| FR | 2 635 955 | 3/1990 |
| WO | WO 98/18503 | 5/1998 |

*Primary Examiner*—Lisa A. Douglas
(74) *Attorney, Agent, or Firm*—Winston & Strawn

(57) ABSTRACT

The present invention is drawn to a device for perfuming ambient air or closed spaces. The said device comprises water or an appropriate hydrophilic solvent containing said volatile active ingredient and an absorbing material chosen from superabsorbents, starch based systems, chemically modified cellulose and natural gum and which are capable of forming a gel with water or said hydrophilic solvent, both components being adapted to be mixed with each other in order to achieve the diffusion of said volatile ingredient from the said gel. The components are mixed with each other to form said gel from which the perfume or a deodorizing or sanitizing agent, or an insect repellent, diffuses uniformly and over a prolonged period of time into the surrounding air.

33 Claims, 4 Drawing Sheets

Fragrance eminated by 2 different air-fresherners

GEL TYPE VAPOR RELEASE DEVICE

This application is a continuation of International Application No. PCT/IB99/01721 filed on Oct. 20, 1999, the content of which is expressly incorporated herein by reference thereto.

TECHNICAL FIELD AND PRIOR ART

The present invention relates to the field of perfumery. It relates, more particularly, to a gel device which allows for an effective and prolonged evaporation of an active volatile substance, like a perfume, an insect repellent or a deodorizing or sanitizing agent.

The use of various devices for the diffusion of volatile compounds, for example perfumes, sanitizing agents, insect repellents, and the like, has become more and more current in recent years. For example, air-freshening devices or deodorizers are currently used in practically all households to mask bad odors or to impart fragrances to the ambient air. The known devices used for the diffusion of volatile compounds into the surroundings make use of various principles. As an example, one can mention here dispersing devices of the spray type, aerosols or mechanical. Other examples include plastic packing elements enclosing the active ingredients in liquid form. Typically, the diffusion of the active ingredient takes place through membranes permeable to the vapors of said ingredient.

One class of systems capable of diffusing active volatile ingredients are solid state devices consisting of solid materials or carriers impregnated with an active ingredient. Such devices may be formed of various materials which are capable of absorbing the ingredient and subsequently releasing it in a more or less controlled manner. Examples of such known materials include gels, such as agar-agar or sodium stearate gels, synthetic polymer resins, or blocks of mineral material, e.g. plaster or silica. It is even possible, for some purposes, to have active ingredients absorbed on paper or cardboard in order to obtain a more or less solid carrier device for diffusing the volatile ingredient thus absorbed. Often, solid devices are designed to be non-wetting, i.e. to be capable of effectively retaining the liquid active volatile material and only allowing the diffusion of the vapors of said material.

In general, diffusing devices are to be activated by the customer. Such devices often comprise a pouch or sachet containing the active ingredient and which is hermetically sealed. In order to release the ingredient, the customer will have to pierce the sachet, make it burst or peel off a certain part of it in order to let the active ingredient escape into the surroundings. Other devices comprise multiple compartments having a rupturable joint between them, at least one of these compartments being of a material which is not permeable to the vapors of the ingredient and the other being permeable. Devices of this kind are activated by applying pressure to the non-permeable compartment, upon which the rupturable joint opens to let the active ingredient flow into the compartment which is permeable to its vapors. A diffusing device of this kind is described in U.S. Pat. No. 4,798,288, for example.

Despite prior known diffusing devices for active volatile ingredients, there is still a need for diffusing devices which are capable of releasing effective amounts of active ingredient into the surroundings, in general closed spaces, and this for a prolonged period of time.

DESCRIPTION OF THE INVENTION

According to the invention this object is attained by a device for the diffusion of a volatile active ingredient, comprising an appropriate hydrophilic medium, said volatile active ingredient and an absorbing material selected from superabsorbent substances, starch based systems and chemically modified cellulose, said absorbing material being capable of forming a gel with said hydrophilic medium susceptible of enclosing said volatile active ingredient within and of permitting the diffusion of said volatile ingredient from the gel upon exposure of the latter to air.

The invention also relates to a method for the diffusion of active volatile substances into ambient air, in particular air in closed spaces, the method comprising exposing a gel resulting from mixing a solution, emulsion or suspension of a volatile active ingredient in an hydrophilic solvent with an absorbing material selected from superabsorbent substances, starch based systems, chemically modified cellulose and natural gums, so as to form said gel, to air.

We have found that the diffusion systems according to the invention provide a very uniform and prolonged diffusion of the active ingredient.

As active ingredient, there can be used for example perfumes, resulting in air-fresheners. Other suitable active ingredients comprise deodorizing or sanitizing agents, or insect repellents, or yet any other volatile materials capable of imparting perceptible and desirable benefits to the quality of the air into which they are diffused.

The absorbing material according to the present invention, intended to be mixed with the hydrophilic medium, preferably an aqueous solution, emulsion or suspension of the volatile active ingredient is preferably a so-called superabsorbent material or substance. These are materials which are capable of absorbing large amounts of water or other hydrophilic media. In the context of the present invention, superabsorbents are organic synthetic polymers containing acrylic acid or methacrylic acid, or a salt thereof, these polymers being capable of absorbing between about 50 and 200 times their own weight of water or hydrophilic solvent. Amongst the most current superabsorbents one can cite the cross-linked sodium polyacrylate/polyacrylic acid polymers. Superabsorbents of this type are commercially available under the names of Salsorb® (Allied Colloids Ltd.) and Cabloc® (Stockhausen GmbH).

The superabsorbents of the invention, which are in the form of a fine powder, should preferably have a particle size from about 50 to about 500 microns in order to provide a smooth gel upon admixture of the components of the diffusion device. Powders with larger or lower particle sizes than those mentioned can also be used, but they will result in coarser, or, respectively finer, gels.

According to the invention, best results were obtained with the commercial cross-linked sodium polyacrylates sold under the tradename of Salsorb®. However, it goes without saying that the present invention is not limited to the above-specified materials. There can also be used other types of superabsorbents, for example polymers of other salts of acrylic acid or methacrylic acid, polyacrylamides, polyacrylic esters, polymethacrylic esters, copolymers of acrylates, methacrylates, acrylic acid or methacrylic acid with vinyl acetate, vinyl alcohol or maleic anhydride, isobutylene-maleic anhydride copolymers, saponified graft polymers of acrylonitrile or graft polymers of starch and acrylic acid.

Yet other absorbing materials which can be used in the present invention are acrylic polymers other than those cited above, e.g. acrylamide polymers, starch based systems, e.g. cellulose, gluten, chemically modified cellulose, e.g. carboxymethylcellulose, or cellulose ethers.

The absorbing material as specified above is mixed with a hydrophilic solvent, preferably water or a water based medium possibly containing a small amount of ethanol or a similar solvent, and the volatile active ingredient. In general, the hydrophilic solvent will contain the volatile active ingredient. To this end, there will in general be used a solution, suspension or emulsion of the active ingredient in said hydrophilic solvent.

The hydrophilic solvent is an essential element of the present invention. Its presence is mandatory to achieve the desired regular and prolonged evaporation of the active ingredient. It can be said that said solvent acts as an evaporation aid. Without the presence of the solvent, the evaporation of the active ingredient generally occurs at such a low rate that an effective working of a device according to the present invention is not assured. A further advantage is that a uniform distribution of the active ingredient in the absorbing material is achieved.

When said solution, suspension or emulsion is prepared, it may be advantageous to use an emulsifying agent, although this is optional. In general, a surfactant will be used as emulsifying agent. Systems have been prepared and found to function satisfactorily without the use of a surfactant, where the active volatile ingredient, e.g. perfume, and the water are held in suspension by the gelled structure. Where surfactants are used, nonionic surfactants are preferred. Examples of this class of surfactants include ethoxylated sorbitan esters which are available under the trade names Span® (origin: ICI) and Brij® (origin: ICI). Ethoxylated saturated fatty esters like those sold under the names of Cremophor® (origin: BASF) and Lutensol® (origin: BASF) can also be used. Further examples of appropriate nonionic surfactants include alcohol ethoxylates, polyethylene glycol esters and ethylene oxide/propylene oxide copolymers. These surfactants can be present in the aqueous solution, emulsion or suspension of the active ingredient in concentrations varying from 0 to 10% by weight, preferably from 1 to 3% by weight, relative to the total weight of said resulting solution, emulsion or suspension.

As mentioned above, the active ingredient which will be diffused by the device of the invention can typically be a perfuming ingredient, a deodorizing or sanitizing agent or an insect repellent.

As a perfume or perfuming ingredient there can be used in the device of the invention any ingredient or mixture of ingredients currently used in perfumery. The latter can be made of discreet chemicals; more often, however, it will be a more or less complex mixture of volatile ingredients of natural or synthetic origin. The nature of these ingredients can be found in specialized books of perfumery, e.g. in S. Arctander (Perfume and Flavor Chemicals, Montclair N.J., USA 1969) or similar textbooks of reference, and a more detailed description thereof is not warranted here.

Although special mention has been made hereinabove of the perfuming effect that can be exerted by the invention device, the same principles apply to the manufacture of analogous devices for the diffusion of deodorizing or sanitizing vapors, the perfume base being then replaced by a deodorizing composition, a bactericide, an insecticide, an insect repellent or even an insect attractant. By the term "sanitizing vapors", we refer here not only to the vapors of those substances which can enhance the degree of acceptance of surrounding air to the observer, but also to those substances which can exert an attractant or repellent effect towards certain species of insects, for instance towards houseflies or mosquitoes, or else, which can have bactericide or bacteriostatic activity. It goes without saying that mixtures of such agents can also be used.

The above-identified compounds will be admixed with the water or an appropriate hydrophilic solvent in a quantity which can range, for all types of gels, from about 0.1% to about 15% by weight of the resulting solution, emulsion or suspension, preferably about 1 to 6% by weight. Upon use of superabsorbents, these values may slightly differ from those above which are valid for conventional absorbing media. We found that the incorporation of larger amounts of active ingredient is possible. For superabsorbents of the sodium polyacrylate/polyacrylic acid polymer type, values from about 0.1% to about 20% by weight of active ingredient in the solution, emulsion or suspension can be attained, the preferred range being from about 1% to about 6% by weight. It is clear that in cases where small amounts, such as for example 0.1%, are used, there will often be observed only a minor effect and the lifetime of the device will be considerably short. The upper limit for the amount of active ingredient that can be used, on the other hand, shall be determined by the ability of the absorbing material to absorb the solution.

The absorbing material and the solution, emulsion or suspension containing the active ingredient will be mixed together in order to form the gel device capable of releasing the ingredient. When a superabsorbent is used as absorbing material, it will be present in an amount of from about 0.1% to about 15%, preferably from about 2% to 5% relative to the total weight of the resulting gel, the balance being the weight of the solution, emulsion or suspension containing the ingredient.

The gel obtained after mixing the absorbing material with the hydrophilic solution, suspension or emulsion containing the active ingredient, diffuses the active ingredient uniformly and over a prolonged period of several weeks, unlike prior known diffusion devices. Moreover, the device can also provide a use-up cue when all the active ingredient is exhausted and the absorbing material is formed of a superabsorbent substance. Such superabsorbent materials (which before mixing are in the form of a fine powder), do in fact shrink from the gel form into a conglomerate of the originally present particles upon exhaustion of the volatile active ingredient. The appearance of these materials can then be described as being that of wet opaque crystals sticking to each other and the used-up article therefore is easily distinguishable from the gel originally obtained upon mixing the components mentioned before.

The end point cue is even more visible when a water-soluble dye is incorporated into the dry superabsorbent, i.e. before mixing the latter with the solution, emulsion or suspension of the volatile ingredient in the hydrophilic medium. Before activation of the device, the dye is not distinguishable from the superabsorbent powder. Yet, when the superabsorbent containing the dye is mixed with the solution, emulsion or suspension of the active ingredient, the dye colors, as a consequence of the presence of water and the distribution of the dye in the gel, thus giving the user a clear indication that the diffusion device is now activated. The presence of the dye also facilitates the recognition of the end point of the device, due to the change between the original gel and the particles forming upon exhaustion of the diffusion device. A further advantage of the presence of the dye is that the user can follow the mixing or activation process of the device of the invention with his eyes thanks to the color appearance. Only quite low amounts of dye are necessary to obtain the desired effects, and typical concentrations are from about 0.01% to about 1%, preferably 0.1% by weight, relative to the weight of the superabsorbent.

An advantage of the device according to the invention is that, after exhaustion, it can be easily replenished simply by adding a fresh emulsion or solution containing an active ingredient to the used up material. The device will then function practically as good as a device which has been activated for the first time.

The activation of an air-freshening device according to the present invention can be accomplished in different ways.

In one embodiment of a device of the invention, the absorbing material and the solution, emulsion or suspension containing the active ingredient are separated from each other. The customer, after buying these two components, activates the device simply by mixing the components, resulting in an air-freshener which gives the described prolonged diffusion of active ingredients.

Air-freshening devices according to a further embodiment of the present invention already contain the gel resulting after admixture of the absorbing material and the solution, emulsion or suspension containing the active ingredient. The container in which the gel is found is sealed, in order not to allow diffusion of the active ingredient into the surroundings. The customer will then activate the device simply by opening the container, after which the active ingredient will evaporate. This embodiment is possible because the gels obtained after mixing of the above-mentioned ingredients are perfectly stable for a period of several months and can hence be stored.

According to a preferred embodiment of the invention, the diffusing device shall comprise separate compartments for the absorbing material and for the hydrophilic medium containing the volatile active ingredient, means being provided to permit the activation or mixing step being carried out by the user himself. The two above-mentioned components can e.g. be in the form of two closed, separate and preferably transparent containers, each containing one of the components. The user can then open both containers and activate the diffusion device by mixing the components. In a preferred embodiment, the components will be arranged in a packing having at least two compartments and a rupturable joint or wall common to both compartments. The components are each separately lodged in one of the said compartments. The two components can then be mixed by rupturing or bursting the joint or wall, for example by applying pressure to at least one of the compartments. The two components can subsequently be easily mixed by shaking the package. A top layer or closure covering at least a part of the compartment will then be removed to allow the diffusion of the active ingredient into the surrounding air. A package of this type, used for a different purpose, is described for example in U.S. Pat. No. 4,798,288, the content of which is hereby included by reference. The person skilled in the art of air-fresheners will appreciate that many other types of commonly used air-freshener packages will fulfill the objective of the invention.

In another preferred embodiment of the invention, at least a part of the wall of the compartment containing the absorbing material is permeable to the vapors of the active ingredient, closure being then not necessary. When the joint between the compartments is broken, the solution, emulsion or suspension containing the active ingredient will flow into the compartment containing the absorbing material, forming a gel. The active ingredient can then diffuse into the surrounding air through the walls of the compartment, the removing of a top layer or closure not being necessary in this particular case.

In a further preferred embodiment of the air-freshener device according to the present invention, said device comprises a reservoir containing an appropriate hydrophilic solvent. The gel is located in the upper part of said reservoir. Means are provided to ensure an appropriate supply of a hydrophilic solvent to the gel. As hydrophilic solvent, there will be used the same liquids as for the preparation of the solution, emulsion or suspension containing the active ingredient. The most preferred hydrophilic solvent is water.

By this, the gel will remain completely moistened by the liquid throughout its whole lifetime, i.e. until all active compound has evaporated. As mentioned above, it was found that the hydrophilic solvent, in particular water, acts as an evaporation aid for the active ingredient. There is observed a lower evaporation rate for said active ingredient if the gel is not properly moistened, respectively hydrated, by a hydrophilic solvent, even if there remains an amount of active ingredient in the gel which should not yet give rise to said lower evaporation rate. By keeping the gel sufficiently moistened, an efficient and complete evaporation of the active ingredient is ensured, resulting in a prolonged lifetime of the air-freshener.

Devices for providing an appropriate supply of hydrophilic solvent to the gel are known to a person skilled in the art. For example, one possibility is to provide said supply by capillary action. Simple capillaries or small tubes, made from, for example, glass or plastics, often give sufficient results. The best results, however, were obtained by using a wick. Of course, the material and dimensions of such wick must be chosen in a way that a sufficient amount of solvent is supplied to the gel to keep it entirely moistened. The necessary amount depends on the amount of gel and its absorbing properties.

A large number of organic and inorganic materials can be used for the wick. Examples for appropriate inorganic materials include porous porcelain material, glass fiber, or asbestos, in combination with a suitable binder such as, for example, gypsum or bentonite. It is also possible to prepare wicks from powdered mineral materials, such as, for example, clay, talc, kieselguhr, alumina, silica or the like, singly or in combination with, for example, wood flour, carbon powder, or activated carbon, using an appropriate glue. Organic materials include felt, cotton, pulp, woven and non-woven cotton fibers, woven and non-woven synthetic fibers, and porous polymeric foams and sponges.

We could obtain particularly advantageous results with a wick consisting of a polyester filling surrounded by perforated polypropylene. Such a material is commercially available at Baumgartner Papier SA, Switzerland.

The wick must be able to transport the hydrophilic solvent, in general water, at least as quick to the gel as the solvent evaporates from the surface of the gel.

As mentioned above, in this embodiment of an air-freshener according to the present invention, the gel will be in a container adjacent to the reservoir and connected to it by an appropriate supply, preferable a wick. It is preferred when the gel sits on a piece of absorbing material connected to the wick, like thick, absorbent paper, for example filter paper, in order to ensure a regular distribution of the solvent in the gel.

The container which takes up the gel is covered by a material which is permeable to the vapors of the active ingredient, in order to prevent the gel from falling out. To this end, a mesh may be used.

The material permeable for the vapors is sealed by an appropriate closure which can easily be removed by the customer after purchase, in order to activate the air-freshening device according to the present invention.

In this preferred embodiment of an air-freshener according to the present invention, it is possible to simply add new water to the reservoir once it is empty, as long as there remains active ingredient in the gel. By this, it is for example possible to incorporate larger amounts of fragrance in the gel and provide air-freshening device with a prolonged lifetime in which the reservoir simply has to be refilled from time to time by the customer to keep the device working.

After activation, the gel of the diffusion device of the invention should preferably have an evaporation surface of from about 10 to about 60 cm$^2$, preferably of from about 20 to about 40 cm$^2$, in order to allow an effective diffusion of the active ingredient.

The device of the present invention allows a linear and effective release of fragrance, with only low amounts of fragrance remaining in the gel after exhaustion of the perfume or the other active ingredient.

The invention will now be described in further detail by way of the following examples.

EMBODIMENTS OF THE INVENTION

EXAMPLE 1

Perfuming compositions were prepared by admixing the following ingredients, in a variety of proportions within the ranges indicated.

| Ingredients | Range of concentrations % by weight |
|---|---|
| Dipropylene glycol | 50–70 |
| Isobornyl acetate | 5–20 |
| Terpineol | 1–5 |
| Eucalyptus oil | 0.2–3 |
| Methyl nonyl aldehyde | 0.2–3 |
| Dihydromyrcenol | 1–8 |
| Terpinyl acetate | 0.5–5 |

By using anyone of the perfumes thus obtained, air-fresheners according to the invention were prepared with the following ingredients, in the proportions indicated:

| | % by weight of gel | | |
|---|---|---|---|
| Ingredient | Gel 1 | Gel 2 | Gel 3 |
| Deionised water | 92 | 89 | 95 |
| Perfume | 3 | 6 | 3 |
| Non-ionic surfactant | 3 | 3 | — |
| Salsorb ® | 2 | 2 | 2 |
| Water soluble dye * | trace | trace | — |

* D&C Green N° 5 from D. F. Anstead Ltd. UK

Typically, the Salsorb® containing 0.1% of its weight of water soluble dye uniformly distributed within was added to the previously prepared emulsion of the perfume (3% of total emulsion) in the water containing the surfactant (3% of total emulsion), which had been placed in a glass container, for example a small bottle or flask of appropriate size. Upon admixture, a very soft gel immediately formed which remained firmly in the flask even if the latter was turned upside down.

Similar gels could be obtained in plastic containers of any desired form, which, upon setting of the gel, could be covered with a grid permitting evaporation of the perfume contained in the gel.

Figure 1:
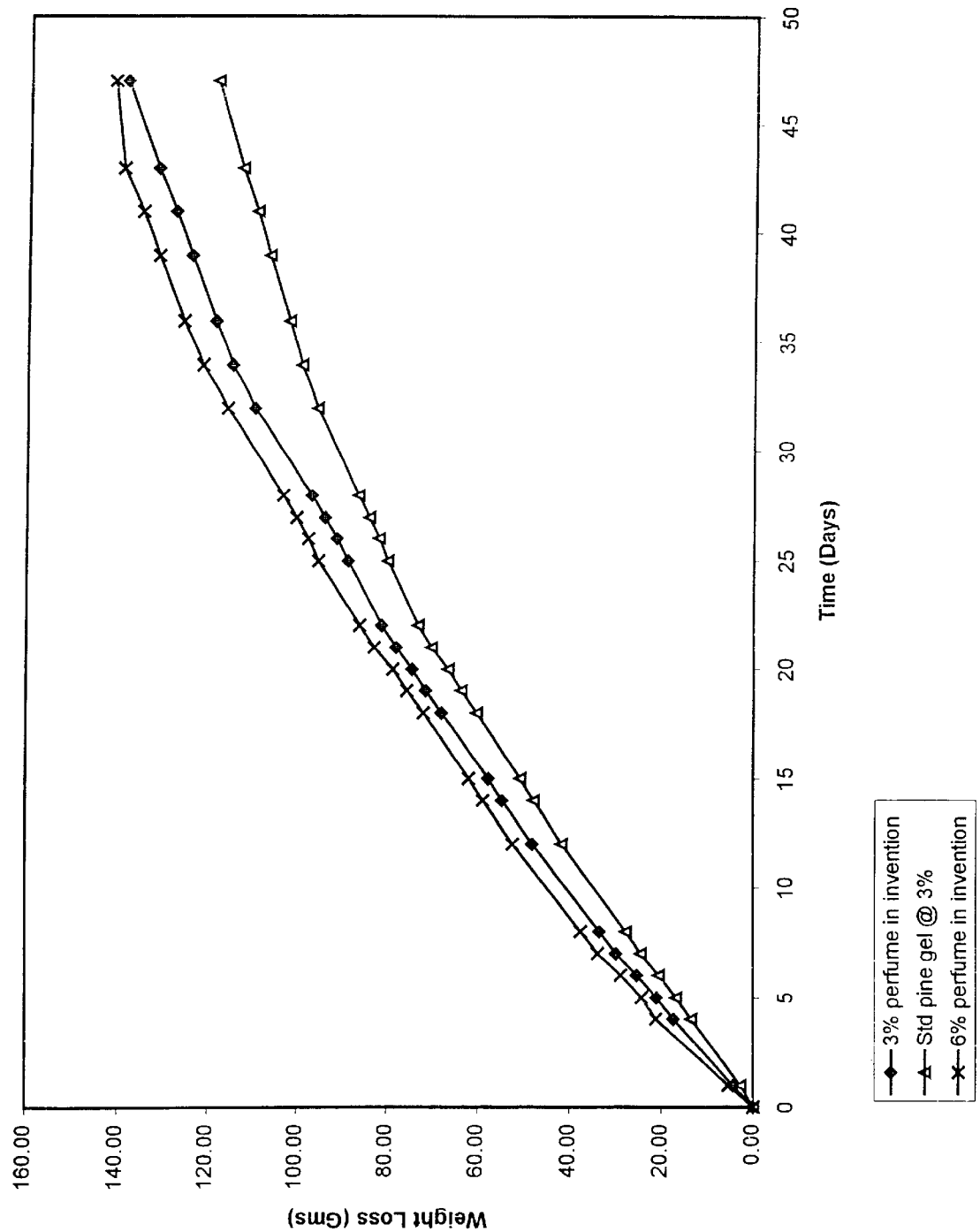
FIG. 1 represents the weight loss, as a function of time, of two gels according to the invention, in comparison with that of a standard carrageenan gel.

FIG. 1 shows the evolution in time of the weight loss suffered by two gels according to the invention (gels 1 and 2 above) as the perfume evaporates, in comparison to the behaviour of a standard air-freshener available on the market and based on a standard carrageenan gel containing 3% by weight of perfume. It is apparent from this figure that the gels of the invention consistently release a larger amount of perfume/water over the same period of time. Intensity testing of the gel and headspace analysis consistently shows the fragrancing to be more intense and with improved release of fragrance components, compared to standard gels.

EXAMPLE 2

Figure 2:
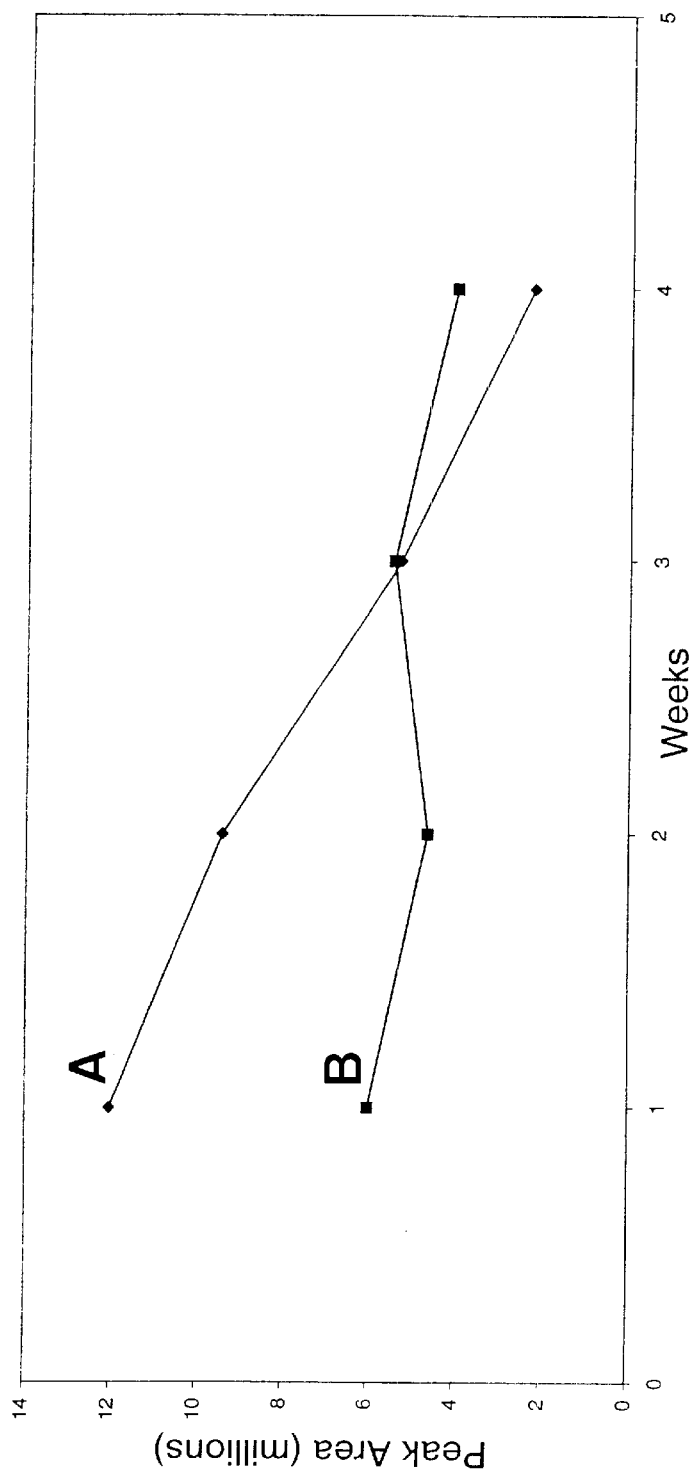
FIG. 2 shows the amount of fragrance emitted by a wick-type air-freshener according to the invention, compared to the amount of the same fragrance emitted by a polyurethane pre-polymer water-based gel, as a function of time.

Perfuming compositions according to those described in Example 1 were used to prepare a wick-type air-freshener with a water reservoir and Salsorb® as absorbing material. There were used 80 g of gel in which there were incorporated 5 g of perfume. 2% by weight of Salsorb® were used. The level of fragrance emanating from the wick system over 4 weeks was compared to the fragrance level emanating from a standard polyurethane pre-polymer water-based gel containing the same fragrance in an identical amount, by a headspace analysis of the SPME (Solid-Phase Micro Extraction) type. The results are shown in FIG. 2, which clearly illustrates that the wick-type air-freshener according to the present invention releases an almost constant amount of fragrance during the 4 weeks. The polyurethane pre-polymer based air-freshener releases a too large amount of fragrance in the beginning, which amount fastly drops to low levels after some weeks.

Figure 3:
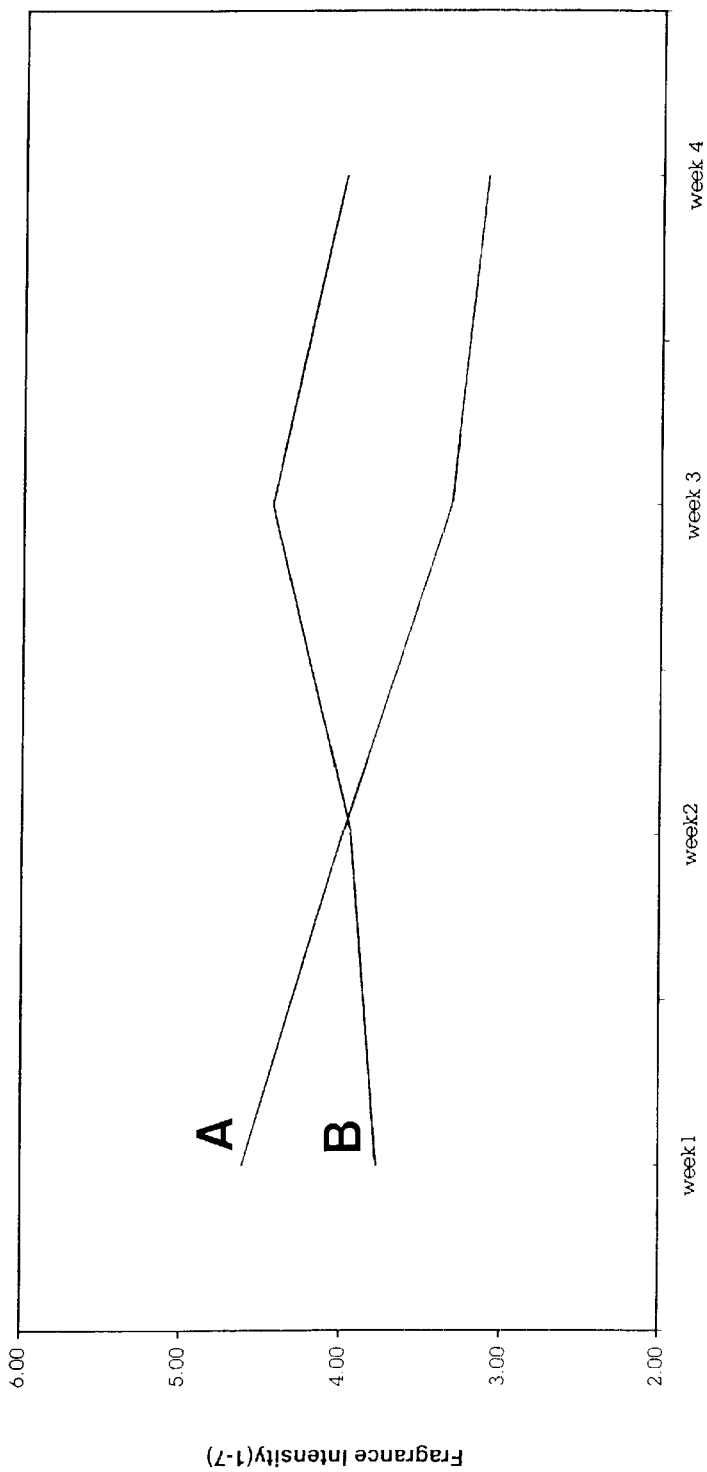
FIG. 3 shows the results obtained from a panel testing the intensity of the fragrance emitted from the two above-identified gels, as a function of time.
Figure 4:
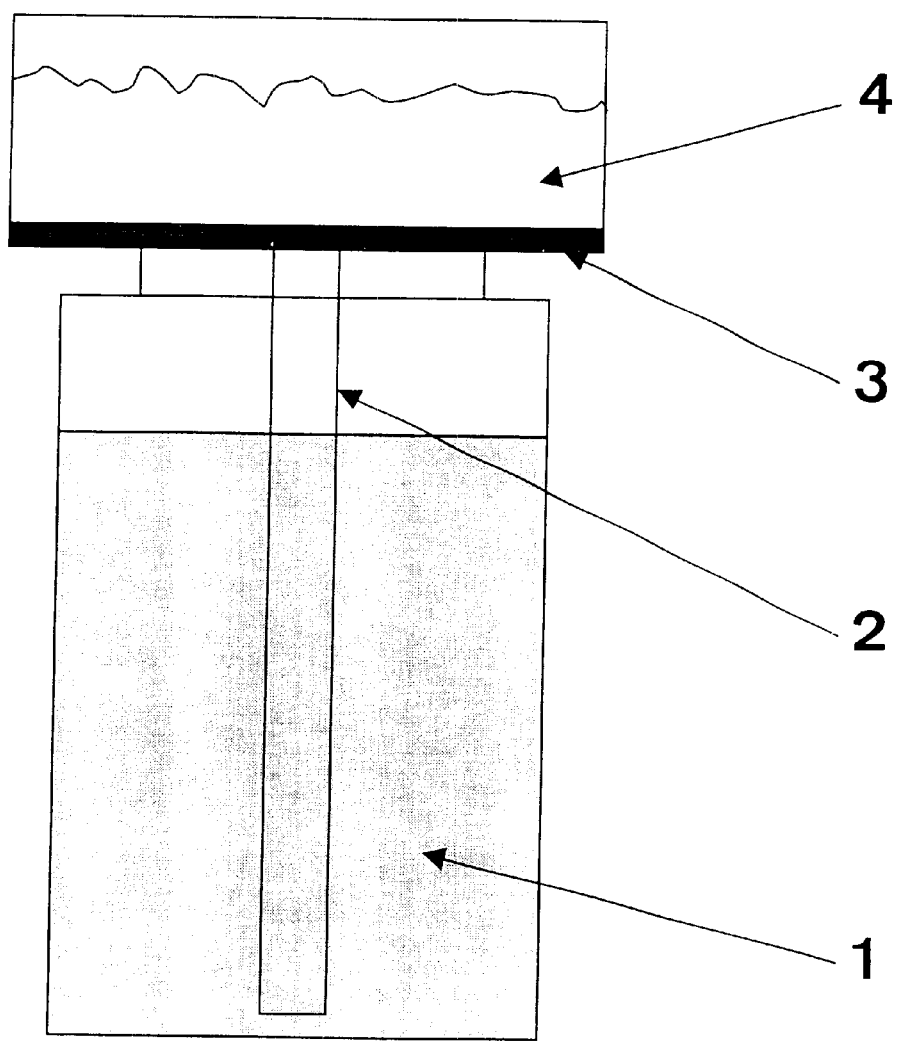
FIG. 4 shows one embodiment of a wick-type air-freshener according to the present invention. A reservoir 1 filled with a liquid, preferably water, a wick 2 providing means to feed the liquid to the gel 4 located in the upper part of the device and keeps it moistened. The gel sits on a piece of filter paper 3 or other material capable of absorbing the liquid and ensuring regular moistening of the gel.

These results were confirmed by a semi-expert panel which rated the intensity of the fragrance emitted by both devices after 1, 2, 3 and 4 weeks on a scale from 1 to 7. The results are shown in FIG. 3. The panel results clearly confirmed that the polyurethane type air-freshener gives an intense odor shortly after it activation, which however drops steadily with time. The wick-type air-freshener according to the present invention, on the contrary, gives a practically constant odor over 4 weeks.

What is claimed is:
1. A device for the diffusion of a volatile active ingredient, which device comprises a container that includes therein:

a) an appropriate hydrophilic medium;
b) the volatile active ingredient; and
c) a superabsorbent substance,
   wherein the superabsorbent substance is capable of forming a gel with said hydrophilic medium and is susceptible of enclosing the volatile active ingredient within the gel as well as capable of permitting diffusion of the volatile ingredient from the gel upon exposure of the latter to air.

2. The device according to claim 1, wherein the hydrophilic medium is water or a water based solvent.

3. The device according to claim 2, wherein the medium forms a solution, emulsion or suspension with the volatile ingredient.

4. The device according to claim 3, wherein the solution, emulsion or suspension of the volatile active ingredient comprises an emulsifying agent.

5. The device according to claim 4, wherein the emulsifying agent is a nonionic surfactant, present in an amount of about up to 10% by weight, relative to the total weight of the solution, emulsion or suspension.

6. The device according to claim 5, wherein the volatile active ingredient is present in the solution, emulsion or suspension in an amount of from about 0.1% to about 15% by weight of the solution.

7. The device according to claim 1, wherein the volatile active ingredient is a perfume, an insect repellent or a deodorizing or sanitizing agent.

8. The device according to claim 1, wherein the gel resulting from the admixture of the active ingredient and the superabsorbent substance has an evaporation surface of from about 10 to about 60 $cm^2$.

9. The device according to claim 1, wherein the superabsorbent substance is a polymer of acrylic acid, methacrylic acid or a salt thereof, a polyacrylamide, a polyacrylic ester, a polymethacrylic ester, a copolymer or acrylates, methacrylates, acrylic acid or methacrylic acid with vinyl acetate, vinyl alcohol or maleic anhydride, an isobutylene-maleic anhydride copolymer, a saponified graft polymer of acrylonitrile or graft polymers of starch and acrylic acid.

10. The device according to claim 9, wherein the superabsorbent substance is a cross-linked sodium polyacrylate/polyacrylic acid polymer.

11. The device according to claim 10, wherein the superabsorbent is a powder having a particle size of from about 50 to about 500 microns.

12. The device according to claim 3, wherein the superabsorbent substance is a sodium polyacrylate/polyacrylic acid superabsorbent material and the amount of active ingredient in the solution, emulsion or suspension is from about 0.1% to about 10% by weight of the solution.

13. The device according to claim 1, wherein the superabsorbent substance is a superabsorbent of the sodium polyacrylate/polyacrylic acid type which is present in an amount of from about 0.1% to about 15% by weight, relative to the total weight of the gel obtained after admixture of the ingredients.

14. The device according to claim 1, wherein the superabsorbent substance absorbs 50 to 200 times its weight in water and contains from about 0.01% to about 1% by weight of a water-soluble dye.

15. The device according to claim 1, wherein the container is composed of two compartments.

16. The device according to claim 15, wherein the superabsorbent substance and hydrophilic medium containing the volatile ingredient are stored in the separate compartments and further comprising means associated with the compartments to allow admixture of the superabsorbent substance with the hydrophilic medium to form the gel.

17. A device according to claim 15, which further comprises a rupturable or burstable joint or wall common to both containers, one of which contains the superabsorbent substance, the other compartment enclosing the hydrophilic medium comprising the volatile active ingredient.

18. The device according to claim 15, wherein the compartment containing the superabsorbent substance has a wall permeable to the vapors of the active ingredient and which wall can be sealed by an appropriate removable closure.

19. A device according to claim 1, wherein the gel is present in the form as obtained after mixing the superabsorbent substance, the hydrophilic medium and the volatile active ingredient.

20. The device according to claim 19, which further comprises a reservoir containing an appropriate hydrophilic solvent and wherein the gel is located in the upper part of the reservoir, means being provided to ensure supply of the hydrophilic solvent to gel so as to maintain the latter moistened.

21. The device according to claim 20, which further comprises a wick to ensure the supply of hydrophilic solvent to the gel.

22. The device according to claim 21, wherein hat the wick is formed of an organic inorganic material.

23. The device according to claim 22, wherein wick is made of polyester surrounded by perforated polypropylene.

24. The device according to claim 20, wherein the container containing the gel is covered by a material which is permeable to the vapors of the active ingredient and which can be sealed by an appropriate removable closure.

25. The method according to claim 8, wherein the activation comprises removing the seal covering the container with the gel.

26. A method for the diffusion of active volatile substances into the surroundings, in particular into closed spaces, which comprises activating the device of claim 1 and exposing the gel to the surrounding air to release the vaporizable substances.

27. A method according to claim 26, wherein the activation is carried out by mixing the superabsorbent substance and the hydrophilic solvent containing the active ingredient.

28. A gel resulting from the mixing of a superabsorbent substance with a hydrophilic medium, and an active volatile ingredient selected from perfumes, insect repellents or deodorizing or sanitizing agents; wherein the gel is susceptible of enclosing the volatile active ingredient within the gel as well as capable of permitting diffusion of the volatile ingredient from the gel upon exposure of the latter to air.

29. The device according to claim 8, wherein the gel has an evaporation surface of from about 20 to 40 $cm^2$.

30. The gel according to claim 28, wherein the hydrophilic medium is water or a water-based solvent.

31. The gel according to claim 30, wherein the superabsorbent substance is a cross-linked sodium polyacrylate/polyacrylic acid polymer.

32. The device according to claim 12, wherein the amount of active ingredient in the solution, emulsion or suspension is from about 1% to about 6% by weight of the solution.

33. The device according to claim 13, wherein the superabsorbent substance is present in an amount of from about 2% to about 5% by weight, relative to the total weight of the gel obtained after admixture of the ingredients.

* * * * *